(12) United States Patent
Drevik et al.

(10) Patent No.: US 7,166,093 B2
(45) Date of Patent: Jan. 23, 2007

(54) ABSORBENT ARTICLE WITH REAR PORTION INCLUDING A FIRST AND SECOND LEG

(75) Inventors: Solgun Drevik, Mölnlycke (SE); Fredrik Asp, Onsala (SE)

(73) Assignee: SCA Hygiene Products AB, Gothenburg (SE)

( * ) Notice: Subject to any disclaimer, the term of this patent is extended or adjusted under 35 U.S.C. 154(b) by 127 days.

(21) Appl. No.: 10/003,308

(22) Filed: Dec. 6, 2001

(65) Prior Publication Data

US 2002/0068915 A1 Jun. 6, 2002

Related U.S. Application Data

(60) Provisional application No. 60/251,386, filed on Dec. 6, 2000.

(51) Int. Cl.
*A61F 13/15* (2006.01)
*A61F 13/20* (2006.01)

(52) U.S. Cl. .................. 604/385.101; 604/385.01; 604/385.27

(58) Field of Classification Search ........... 604/385.01, 604/385.27, 385.23, 385.31, 385.101
See application file for complete search history.

(56) References Cited

U.S. PATENT DOCUMENTS

| | | | | |
|---|---|---|---|---|
| 4,804,380 A | * | 2/1989 | Lassen et al. | 604/385.17 |
| 5,300,053 A | * | 4/1994 | Genaro | 604/378 |
| 5,514,104 A | | 5/1996 | Cole et al. | |
| 5,624,422 A | * | 4/1997 | Allen | 604/385.23 |
| 6,198,019 B1 | * | 3/2001 | Hansson et al. | 604/378 |
| 6,425,890 B1 | * | 7/2002 | Samuelsson et al. | 604/385.17 |
| 6,492,574 B1 | * | 12/2002 | Chen et al. | 604/378 |
| 6,565,547 B1 | * | 5/2003 | Bissah et al. | 604/385.01 |
| 6,592,561 B1 | * | 7/2003 | Simard et al. | 604/385.04 |
| 6,740,069 B1 | * | 5/2004 | Drevik | 604/385.01 |
| 6,802,832 B1 | * | 10/2004 | Hansson et al. | 604/385.01 |
| 2001/0039407 A1 | * | 11/2001 | Widlund | 604/385.01 |
| 2002/0052589 A1 | * | 5/2002 | Strand | 604/385.01 |
| 2002/0065497 A1 | * | 5/2002 | Kolby-Falk | 604/368 |
| 2002/0156443 A1 | * | 10/2002 | Drevik et al. | 604/385.01 |
| 2002/0156450 A1 | * | 10/2002 | Drevik et al. | 604/385.101 |
| 2002/0165512 A1 | * | 11/2002 | Drevik et al. | 604/380 |
| 2002/0165513 A1 | * | 11/2002 | Drevik et al. | 604/385.01 |

FOREIGN PATENT DOCUMENTS

| | | |
|---|---|---|
| EP | 0 136 524 | 4/1985 |
| EP | 0 302 523 | 3/1989 |

(Continued)

*Primary Examiner*—Michele Kidwell
(74) *Attorney, Agent, or Firm*—Young & Thompson

(57) ABSTRACT

An absorbent article has a substantially elongated shape with a longitudinal direction and a transverse direction and exhibits two side edges a front edge and a rear edge a front portion and a rear portion and a central portion situated between the front portion and the rear portion The article furthermore exhibits a liquid-pervious cover layer and a liquid-impervious cover layer and an absorbent body. The rear portion of the absorbent body includes a layer that is split in a first leg and a second leg with a gap between the legs, where an angle α is defined between the first leg and the second leg, and an elastic member is placed between the first leg and the second leg, which elastic member essentially extends in the longitudinal direction.

14 Claims, 2 Drawing Sheets

FOREIGN PATENT DOCUMENTS

| | | | |
|---|---|---|---|
| EP | 0 613 671 A2 * | 9/1994 |
| EP | 0 965 318 | 12/1999 |
| GB | 2319185 A * | 5/1998 |
| WO | WO 96/20669 * | 7/1996 |
| WO | WO 97/07764 | 3/1997 |
| WO | 9822061 * | 5/1998 |
| WO | 9822062 * | 5/1998 |
| WO | 9925282 * | 5/1999 |
| WO | WO 99/25282 | 5/1999 |

* cited by examiner

ABSORBENT ARTICLE WITH REAR PORTION INCLUDING A FIRST AND SECOND LEG

TECHNICAL FIELD

The invention relates to an absorbent article such as a sanitary napkin, an incontinence guard, a diaper, or a pantyliner, which article has a substantially elongated shape with a longitudinal direction and a lateral direction and exhibits two side edges, a front edge and a rear edge, a front portion and a rear portion, and a central portion situated between the front portion and the rear portion, which article further exhibits a liquid-pervious surface layer and a liquid-impervious surface layer and an absorbent body.

BACKGROUND ART

Conventional absorbent articles of the type mentioned above usually have a flat shape. Since the female pubic region does not have a corresponding flat appearance, problems can occur when applying and wearing such articles. The contact of the article against the body is not optimum, and when a gap develops there is a great risk of leakage. In order to solve this problem, it has been proposed to make the absorbent articles cup-shaped rather than flat. By and large, this shape provides a better fit to the contours of the body. The cup shape is produced, for example, by arranging an elastic member in the longitudinal edges of the article, or the article is molded in a cup shape in a more or less stiff material.

A problem with articles of the above-mentioned type is that they do not adapt to the anatomy of the user particularly well, but simply have a general cup-shaped appearance. An article shaped in this way does not provide a good fit against the body. In addition, a gap can easily occur between the user's body and the user's briefs since most women, during menstruation, wear briefs which are of poor quality from the outset or are of poor quality because they are old and worn. Unless either the absorbent article or the briefs are able to maintain a good contact with the user's body, there is a great risk of menstruation fluid leaking past both the absorbent article and the briefs.

WO 97107764 discloses an incontinence product having longitudinally extending elasticated means providing a longitudinal ridge in the central portion of the product, by bending the absorbent body and thereby the whole absorbent article. The product has a generally curved shape in the longitudinal direction and is stated to provide improved body contact in the central area of the product.

Even though the longitudinal ridge provides improved body contact in the central portion of the article, a problem with a construction of the type mentioned is that the elastic member bends the absorbent body in the central area only and that the ridge is located only in the central area, and thereby allowing body fluids to migrate between the buttocks of the user when the user is lying down on her back.

It is also known from WO 99/25282 an absorbent article where an elastic member is arranged in the article and gives the article a cup-shaped part at one end portion and a ridge-like elevation at the other end portion. The elastic member may be arranged in a loop in the front portion, which has a cup-shaped part, and where the elastic member in a loop contributes to giving the front portion its cup shape. The elastic member may also be arranged as a continuous thread or band running through the entire article, and in order to further improve the anatomical fit against the user's body for an article with a ridge-like elevation, which extends across both the central portion of the article and across the rear portion thereof, the ridge-like elevation in the end portion has a steeper inclination towards the center line of the article than does the ridge-like elevation in the central portion, as seen from a long side of the article. The cup shape of the front portion will surround the mons pubis during use, and the ridge-like elevation of the rear portion will fit in the cleft between the user's buttocks.

Even though the ridge-like elevation, which extends across both the central portion of the article and across the rear portion thereof, provides improved body contact in the central portion and the rear portion of the article. A problem with a construction of the type mentioned is that the elastic member bends the entire absorbent body. If the absorbent body is too soft, the elastic member bends the article too much, which may result in a bad fit, and if the absorbent body is too stiff the central portion may become bulky and uncomfortable for the user. A bulky or wrinkled ridge-like elevation may not be high enough and/or thin enough to provide sufficient protection for leakage of body fluids between the buttocks of the user when the user is lying down on her back. Another problem is that the ridge-like elevation consists of the thick and relatively stiff absorbent body, which give the ridge-like elevation a triangular shape, which makes the ridge-like elevation relatively wide and thereby hard to fit between the buttocks of a user.

It is also known absorbent articles, which are provided with a deformation element, which causes the article to assume a predetermined shape in response to laterally acting forces.

A problem with deformation elements is that they are expensive and are time consuming and difficult to apply to the article.

Whilst previously known absorbent articles provide relatively good leakage protection and relatively good fit, a need still exists for an absorbent article which further increases the comfort by being small and flexible, and also further reduces the risk of leakage of body fluids between the buttocks of a user lying down on her back, and that the article still is easy and cheap to manufacture. It is therefore an object of the present invention to provide an absorbent article that meets these requirements.

DISCLOSURE OF INVENTION

The object of the invention is to remedy the above mentioned problems and to make available an absorbent article which provides a good fit against the user's body, and which article is comfortable to use and that reduces the leakage of body fluids between the buttocks of a user, especially when the user is lying down on her back.

The absorbent article may be a sanitary napkin, an incontinence guard, a diaper, or a panty-liner, which article has a substantially elongated shape with a longitudinal direction and a transverse direction and exhibits two side edges, a front edge and a rear edge. The absorbent article also has a front portion and a rear portion, and a central portion situated between the front portion and the rear portion. The article furthermore exhibits a liquid-pervious cover layer and a liquid-impervious cover layer and an absorbent body.

The invention is characterized in that the rear portion of the absorbent body comprises a layer that is split in a first leg and a second leg, with a gap between the legs. An angle $\alpha$ is defined between the first leg and the second leg. An elastic member is placed between the first leg and the second leg, which elastic member essentially extends in the longitudinal direction.

The elastic member bends the rear portion in a somewhat parabolic shape, which further improves the anatomical fit against the user's body. When the elastic member bends the rear portion, parts of the absorbent article that lies between the first leg and the second leg will be deformed in such way so as to give rise to the forming of a ridge-like elevation between the first leg and the second leg.

The elastic member runs mainly along a center line of the absorbent article, from a point in the vicinity of where the center line meets the rear edge, to a point beyond the point where the layer in the absorbent body is split into the two legs. The elastic member may run mainly along the center line through the entire absorbent article.

The elastic member may be split into two elastic parts or more in the front portion in order to enhance a cup shaped front portion.

The elastic member may be fastened to any of the layers that builds the absorbent article, dependent on wanted features of the absorbent article.

MODES FOR CARRYING OUT THE INVENTION

Figure 1:
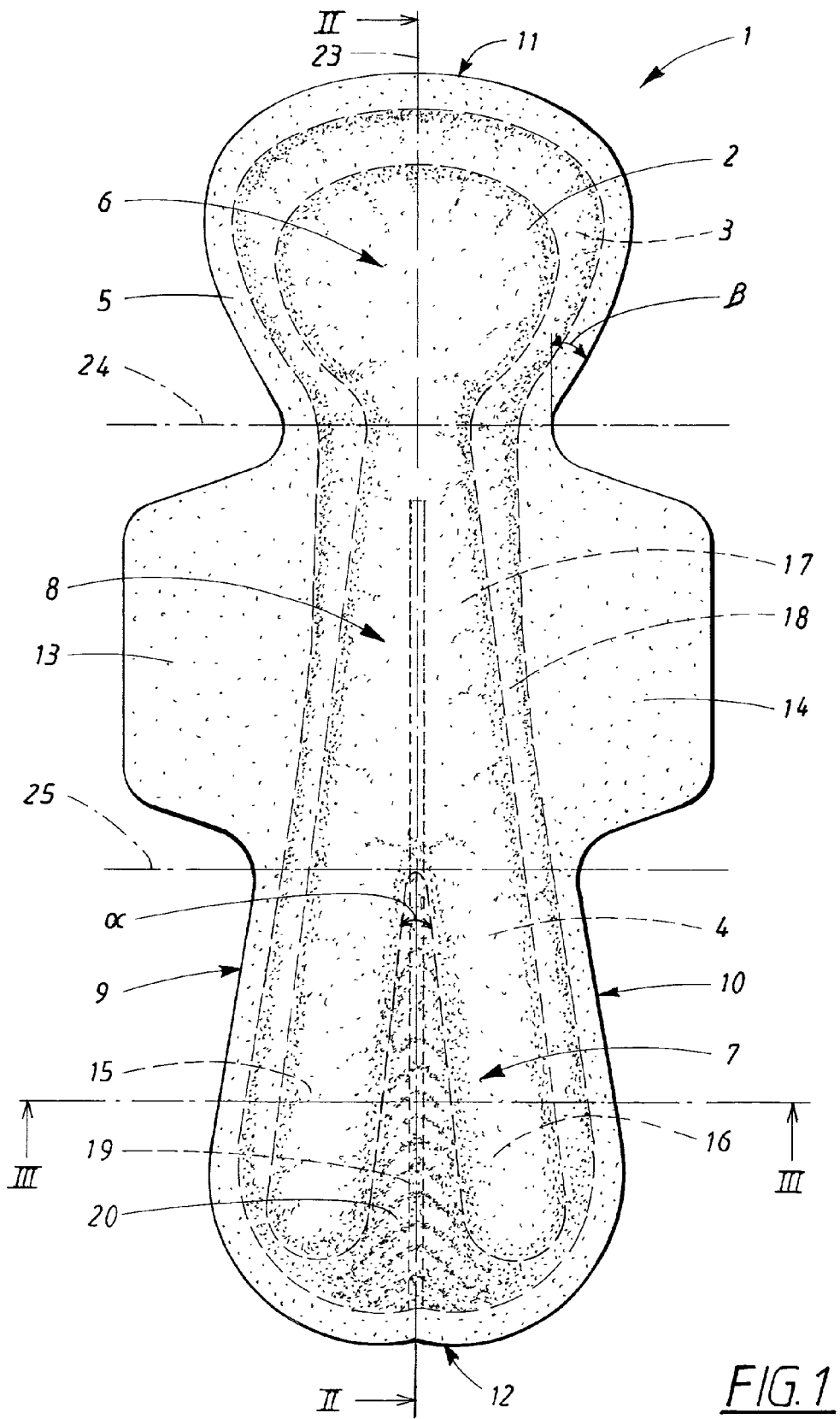
FIG. 1 shows a top view of an absorbent article according to the invention.
Figure 2:
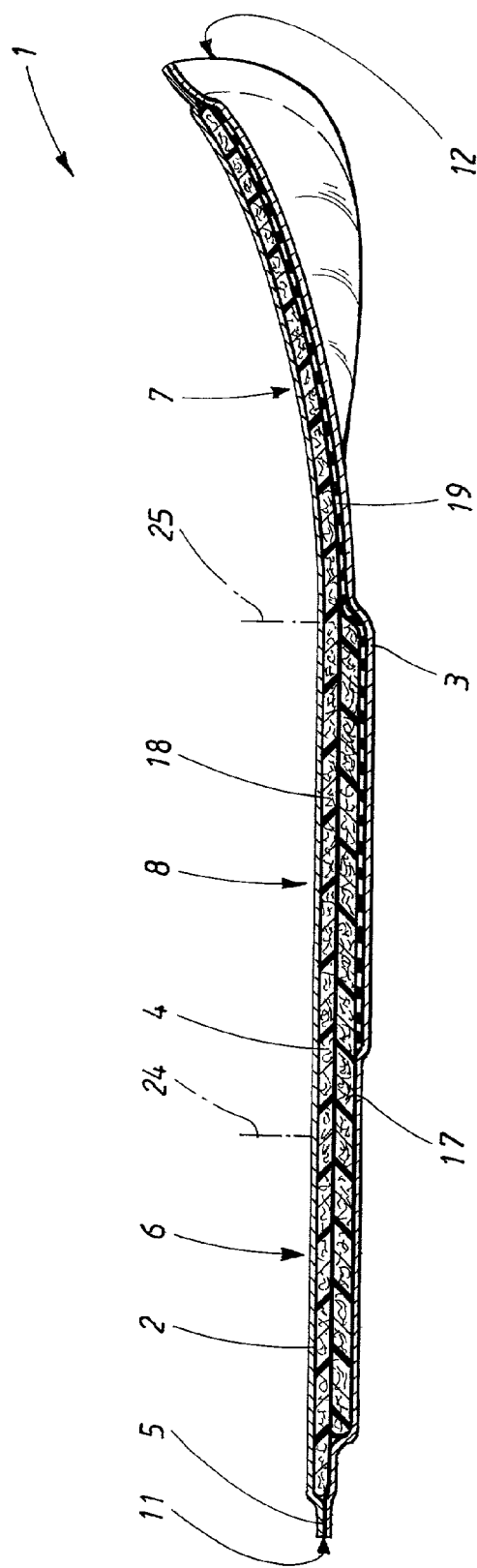
FIG. 2 shows a cross sectional side view of the absorbent article in FIG. 1 taken along a line II—II in FIG. 1.
Figure 3:
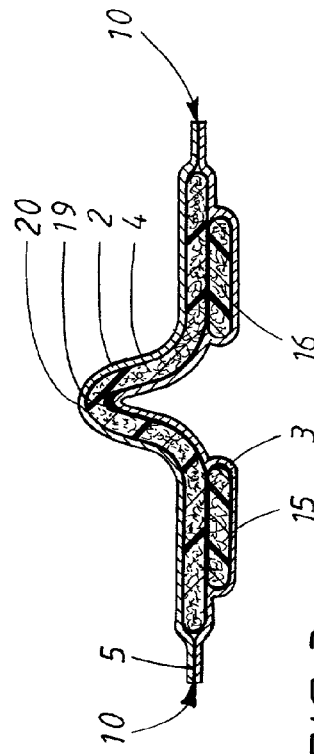
FIG. 3 shows a cross sectional backside view of the absorbent article in FIGS. 1 and 2 taken along a line II—II in FIG. 1.

The absorbent article according to one embodiment of the invention is shown in FIGS. 1, 2 and 3, where FIG. 1 shows a top view of an absorbent article according to the invention, FIG. 2 shows a cross sectional side view of an absorbent article according to the invention, and FIG. 3 shows a cross sectional backside view of an absorbent article according to the invention.

The absorbent article comprises a liquid-pervious cover layer 2 arranged on the side of the absorbent article 1 which, during use, is intended to face the user, a liquid-impervious cover layer 3 arranged on the side of the absorbent article 1 which, during use, is intended to be facing away from the user, and an absorbent body 4 enclosed between the two cover layers 2, 3.

The absorbent body 4 may advantageously comprise different layers of different types of absorbent material. FIG. 1 shows an absorbent body 4 comprising two different layers of absorbent material, a first absorbent layer 17 and a second absorbent layer 18. The first absorbent layer 17 is arranged between the liquid-impervious cover layer 3 and the second absorbent layer 18, and the second absorbent layer 18 is arranged between the first absorbent layer 17 and the liquid-pervious cover layer 2. Advantageously, the second absorbent layer 18 is a fast material that transports fluids well, and the first absorbent layer 17 has a good capacity for storing fluids.

The two cover layers 2, 3 are mutually connected outside the absorbent body 4 and form a protruding edge 5 around the entire periphery of the absorbent article. The joining of the cover layers may take place in any suitable way, such as by means of gluing, sewing, or welding either with heat or ultrasonically.

The absorbent article 1 is substantially hourglass-shaped and thereby exhibits a front portion 6, intended to be directed forward on the user during use, a rear portion 7, intended to be directed backwards on the user during use, and an intermediate, narrower central portion 8 intended to be applied in the groin area of the user. Furthermore, the absorbent article 1 has two concavely curved side edges 9, 10, a convexly curved front edge 11, and a similarly convexly curved rear edge 12.

The segmentation of the absorbent article into a front portion 6, a rear portion 7, and a central portion 8, should not be understood as implying that there are sharp limits between the different portions 6–8, but is primarily intended to facilitate the description of the absorbent article with reference to the differences which are present between the different portions 6–8 depending on how they are intended to be placed in relation to the body of a user. Thus, the transition between the different portions 6–8 does not take place at fixed transverse lines, but rather within transitional areas situated at a distance of approximately one third of the length of the absorbent article from the front edge 11 and the rear edge 12 of the absorbent article, respectively. In this manner, the central portion 8 constitutes the part of the absorbent article which, in use, is intended to receive and absorb the major part of the liquid which during use is emitted to the absorbent article.

The absorbent article 1 according to the described embodiment of the invention is designed with a front portion 6 which is wider than the central portion 8, and with a central portion 8 which is narrower than both the front portion and the rear portion. In order to obtain an absorbent article that has a good fit and that feels comfortable for the user, it is essential that the napkin has a shape which to a very high degree is adapted to the anatomy of the user. Thus, it is of particularly great importance that the width of the first absorbent layer 17 at least in the central portion 8 does not exceed approx. 40 mm. One reason why the front portion 6 is wider than the central portion 8 is that the wider front portion 6 together with the narrower central portion 8 forms around the body of the user, and somewhat "hooks" the absorbent article against the legs of the user, thus makes the absorbent article able to stay in place against the body of the user. The wider front portion 6 is preferably in a somewhat oval shape. One reason for this is that the oval shaped front portion 6, when in use, is bent inwardly forming a cup-shaped bowl, i.e. the upwards bending of the front portion 6, in relation to the central portion 8, does not occur along a sharp folding line, but instead the curvature is continuous in the longitudinal direction of the absorbent article. In this manner, the front portion 6 forms a softly rounded bowl, which conforms very well to the anatomy of the user. Furthermore, the oval shape of the front portion 6 also gives a large absorption area/volume for the absorption body 4.

Furthermore, the absorbent article 1 exhibits two longitudinal side edges 9, 10, a transverse concavely curved front edge II and a transverse convexly curved rear edge 12. The absorbent article is designed in such a way that, in the front portion of the central portion 8, there is a first cross-sectional line 24, extending in the transversal direction of the absorbent article, which intersects the side edges 9, 10 of the absorbent article. At the first cross-sectional line 24, the side edges 9, 10 change inclination in relation to the longitudinal center line 23, whereby the width of the absorbent article increases in a direction towards the front edge 11, whereby the front portion 6 exhibits a maximum width, which exceeds the width of the central portion 8 at the first cross-sectional line 24. The maximum width of the front portion 6 is suitably at least twice the width of the central portion 8 at the first cross-sectional line 24. The inclination of the side edges 9, 10 at the front portion 6 is defined by an angle β between each respective side edge 9, 10 and a longitudinal line parallel to the center line 23, whereby β is between 30° and 90° and whereby the width of the central portion 8 of the first absorbent layer 17 at the first cross-sectional line 24, is between 15 and 45 mm and preferably between 20 and 40 mm. All data mentioned above is mentioned as being valid for the whole absorbent article, but that is only true if the contour of the absorbent article closely follows the contour of the first absorbent layer 17.

According to the described embodiment of the invention the first absorbent layer 17 is more rigid than the second absorbent layer 18. But, the material of the first absorbent layer 17 need not be more rigid than the second absorbent layer 18 per se, i.e. the first absorbent layer 17 may be manufactured in such way that it becomes more rigid than the second absorbent layer 18, for instance by glue lamination of several layers of the same or different material or another suitable choice of manufacturing. The first absorbent layer 17 serves as a formation element, whereby the area of the first absorbent layer 17 that lies substantially within the area of the rear portion 7 is split into a first leg 15 and a second leg 16 from a point in the vicinity of a second cross-sectional line 25. Said second cross-sectional line 25 extends in the transversal direction of the absorbent article, intersecting the side edges 9, 10 of the absorbent article. The legs 15, 16 form an angle α in the point where the legs are split. The angle α between the legs 15, 16 is between 10°–120° preferably 15°–40°, and the length of the legs are between 20–350 mm, preferably 50–150 mm. The second cross-sectional line 25 is placed in the imaginary area where the rear portion 7 meets the central portion 8.

The invention is primarily based on that an elastic member 19 is placed between the first leg 15 and the second leg 16, as a continuous thread or band running mainly along the center line 23, from a point in the vicinity of where the center line 23 meets the protruding edge 5 on the rear edge 12 to a point beyond the point where the first absorbent layer 17 of the absorbent body 4 is split into the two legs 15, 16. The elastic member is advantageously fastened to the liquid-impervious cover layer 3, either entirely or partially. The two legs 15, 16 consist of the more rigid first absorbent layer 17 and is covered with the second absorbent layer 18. The part where the elastic member 19 runs in the rear portion 7 consists of the less rigid second absorbent layer 18. Both the absorbent layers 17, 18 are enclosed by the liquid-pervious cover layer 2 and the liquid-impervious cover layer 3.

If the article lacks a protruding edge 5, the elastic member 19 is placed between the first leg 15 and the second leg 16, as a continuous thread or band that runs mainly along the center line 23, from a point in the vicinity of where the center line 23 meets the rear edge 12, to a point beyond the point where first absorbent layer 17 of the absorbent body 4 is split into the two legs 15, 16.

The elastic member 19 bends the rear portion 7 in a somewhat parabolic shape, which further improves the anatomical fit against the user's body. When the elastic member 19 bends the rear portion 7, the second absorbent layer 18 and the liquid-pervious cover layer 2 will be somewhat deformed in such way so as to give rise to the forming of a ridge-like elevation 20 between the first leg 15 and the second leg 16. Since the second absorbent layer 18 is less rigid than the first absorbent layer 17, the rigid legs 15, 16 will be drawn together and will not deform significantly in the lateral direction, which enhances the deformation of the less rigid second absorbent layer 18 and the liquid-pervious cover layer 2, thereby giving rise to a well-defined high and relatively narrow ridge-like elevation 20 in the rear portion 7 of the absorbent article 1. The lack of lateral deformation of the legs 15, 16 also gives rise to a unique shape of the ridge-like elevation 20, where the ridge-like elevation 20 starts from the inside edges of the relatively flat legs 15, 16, seen from the cross sectional backside view in FIG. 3. The ridge-like elevation 20 rises from the inside edges of the legs 15, 16 in a steep upward inclination towards the center line 23. The ridge-like elevation together with the relatively flat legs 15, 16 may be described as being somewhat in the shape of a cross section of a "Witches' hat" with a cone shaped top standing on a flat brim, which clearly can be seen in FIG. 3. Since the legs 15, 16 are relatively flat in the lateral direction, the ridge-like elevation 20 becomes narrow and high. The ridge-like elevation 20 will therefore fit advantageously in the cleft between the buttocks of the user and will effectively stop and absorb any body fluids that flows between the buttocks, especially advantageously for a user lying down on her back. The relatively flat legs 15, 16 of the absorbent article 20 will serve as a stop against the buttocks of the user, thereby preventing that more of the absorbent article 1 deforms and slides in between the buttocks of the user. The shape of the ridge-like elevation 20 in the rear portion 7 has a steep inclination towards the center line 23 of the article 1, as seen from a long side of the article. The inclination towards the center line 23 improves the anatomical fit against the user's body for an article with a ridge-like elevation, which extends across the rear portion thereof.

The importance of the invention lies in that the area between the legs 15, 16 of the absorbent article 1 is less rigid than the areas surrounding that area, i.e. the legs 15, 16. The absorbent article 1 may be manufactured in a number of different ways dependent on the use and/or user demands. To change the features of the sanitary napkin it is possible to work with a number of parameters, for instance the tension of the elastic member 19, where and how the elastic member 19 is fastened, the angle α between the legs 15, 16 and the relative difference in stiffness between the area situated between the legs and the area surrounding that area. All the mentioned parameters give rise to a number of ridge-like elevations according to the present invention, but in different heights, lengths, widths, inclinations and angles, all dependent on the wanted feature. However, independent of how the parameters are changed, the shape of the absorbent core together with the elastic member 19 and the relative difference in stiffness between the area between the legs 15, 16 and the areas surrounding that area, give rise to the narrow ridge-like elevation 20 in the unique shape of a "Witches' hat" according to the invention, as shown in FIG. 3. It is more important that the ridge-like elevation is narrow than it is high, due to the fact that the most important area to fit the ridge-like elevation 20 into, is the area between the buttocks of a user, in close vicinity to the vaginal area of the user. In prior art it is only known to create a ridge like-elevation by bending the whole absorbent article, which do not give rise to such narrow ridge-like elevation as in the present invention, nor does it create a ridge-like elevation in the form of a "Witches' hat" with all the advantages mentioned above.

The ridge like elevation may be described as having a top portion constituting an upper part of the ridge like elevation and that the width of the ridge-like elevation 20 is 0.1–20 mm, preferably 1–8 mm, at the top portion of the ridge-like elevation (20), and that the length of the ridge-like elevation is at least 10 mm. The width of the ridge-like elevation 20 at the top portion corresponds to the dimension of the elastic members and the dimension of the absorbent layer that covers the elastic member, i.e. the second absorbent layer in the described embodiment.

FIG. 3 shows the legs 15, 16, consisting of the first absorbent layer 17, as lying under the second absorbent layer 18, each leg forming a protruding part towards the liquid-impervious cover layer 3, with a relatively flat lateral liquid-pervious cover layer 2 surface in the area. This is due to the choice of manufacturing. Another choice of manufacturing could as well give rise to protruding parts formed by the legs 15, 16 and the second absorbent layer 18, towards the liquid-pervious cover layer 2, with a relatively flat lateral liquid-impervious cover layer 3 surface in the area, i.e. the opposite of what is shown in FIG. 3. regarding the areas that include the legs.

The material of the liquid-pervious cover layer 2 may, for instance, be a perforated plastic film, a plastic scrim or a textile material, a fibrous wadding, a nonwoven material or a laminate of, for instance, a perforated plastic film and a nonwoven sheet. The laminate may be made of any materials suitable for the chosen purpose. The plastic material is typically thermoplastic, such as polyethylene or polypropylene. The expression "nonwoven material" refers to a nonwoven fibrous web. Suitable nonwoven materials may consist of natural fibers, such as cellulose or cotton, or synthetic fibers such as polyethylene, polypropylene, polyester, polyurethane, nylon or regenerated cellulose. Naturally, it is also possible to use nonwoven materials made from fiber blends.

The liquid-pervious cover layer 2 is intended to receive and conduct the liquid into the absorbent body 4. Furthermore, the cover layer 2 should be soft and pleasant against the body of the user, as well as being able to prevent so-called rewetting, i.e. that absorbed body exudate forces its way back towards the skin of the user. For reasons of comfort, and in order to avoid skin irritation, it is important that the surface on the portion of the absorbent article which contacts the skin of the user be maintained as dry as possible during use. Furthermore, a dry surface on the absorbent article is perceived by the user as being cooler and more pleasant during use, and is both from a purely visual aspect, and when handling the absorbent article when this is to be changed, more attractive than a soiled, wet surface. But, in order to avoid irritation of the mucous membranes in the genital parts, the parts of the absorbent article that are in contact with the mucous membranes preferably may be somewhat moist, for instance parts of the ridge-like elevation 20.

It is not necessary for all embodiments of the invention that the liquid-pervious cover layer 2 does in fact constitute a separate material layer. The liquid-pervious cover layer may, for instance, constitute an integral part of an absorbent body. Thus, it is conceivable that the liquid-pervious cover layer be omitted should the absorbent body comprise an absorbent foam layer or another absorbent material being sufficiently coherent not to disintegrate during use. Furthermore, an absorbent nonwoven material may be utilised, which may be a component of an absorbent body and at the same time constitute a liquid-pervious cover layer.

The liquid-impervious cover layer 3 consists of a liquid-impermeable material. Thin, liquid-impervious plastic films are suitable for the purpose. It is, however, also possible to use materials which are originally liquid-pervious but which have been provided with a coating of plastic, resin, or other liquid-impervious material. In this manner, leakage of liquid from the bottom side of the absorbent article is prevented. The liquid-impervious cover layer 3 may accordingly consist of any material which is skin-friendly and which fulfils the criteria of liquid-impermeability. Examples of materials which are suitable as barrier layers are plastic films, nonwoven materials and different types of laminates. Useful plastic films are, for instance, those that consist of polyethylene, polypropylene, or polyester. Alternatively, the liquid-impervious cover layer 3 may consist of a laminate of a liquid-impermeable plastic layer facing the absorbent body and a nonwoven sheet facing the underclothing of the user. Such a construction provides a leakage-proof barrier layer with a textile feel.

As with the liquid-pervious cover layer 2, it is not necessary that the liquid-impervious cover layer 3 is constituted by a separate layer. Accordingly, it is conceivable that the liquid-impervious cover layer 3 constitutes an integral part of an absorbent material, for instance an absorbent foam layer with a liquid-impervious surface.

The absorbent body 4 may advantageously be primarily constituted by cellulose fluff pulp. The fluff may be present in the form of reels, bales or sheets which are dry shredded or wet formed and transformed in a fluffed state into a pulp mat, with or without the admixture of so-called superabsorbents, which are polymers with an ability to absorb several times their own weight of water or body exudate. Examples of other useful materials are different types of natural fibers such as cotton fibers, peat, or the like. It is, of course, also possible to utilize absorbent synthetic fibers, or blends of natural fibers and synthetic fibers. The absorption material may furthermore include further components, such as liquid-distributing members or binders such as e.g. thermoplastic fibers that have been heat-treated in order to bind short fibers and particles into a coherent unit. It is also possible to utilise different types of absorbent foam materials in the absorbent body 4.

An example is drawn from the testing of the present invention and will be presented in the following text. The material in the first absorbent layer 17 expediently consists of a single layer of High Density Air Laid (HDA) from domestic manufacturing with a stiffness of approx. 5.4 Newton. The second absorbent layer 18 expediently consists of a single layer of 100 g Low Density Air Laid (LDA) with a stiffness of approx. 1.15 Newton. The stiffness is measured according to the CIRCULAR BEND PROCEDURE which is described in EP-A-0 336 578, which publication is hereby included as reference. This described method is a modification of ASTM D 4032-82 and involves simultaneous deformation of a material in several directions, one of the surfaces of the specimen becoming concave and the opposite surface becoming convex. The method thus gives a force value which is a measure of the flexural resistance, or the average stiffness in all directions. In this exemplified embodiment, the relative difference in stiffness between the second absorbent layer 18 and the first absorbent layer 17 gives a ratio of 1.15/5.4, which is the same as approx. 21%. This shall only be seen as an illustration, and shall not be seen as limiting for the invention. A change in the materials will of course give other results, which may advantageously be used in some cases, for instance the fact that the second absorbent layer 18 covers the first absorbent layer 17 also in the rear portion, enhances the difference in relative stiffness between the area between the legs 15, 16 and the area that constitute the legs 15, 16.

The elastic member 19 is pre-stressed before it is attached to the absorbent article 1, with a force between 0.05–0.4 Newton, preferably between 0.1-0.3 Newton.

In a further embodiment of the invention (not shown) the elastic member may also be arranged as a continuous thread or band running through the entire absorbent article 1 in order to bend also the front portion and the central portion in a parabolic shape, which enhances the fit against the body of the user as well as enhancing the "hooking" of the front portion 6 against the legs of the user, which enhances the ability of the absorbent article to stay in place during use. Depending on how the elastic member 19 is fastened in the absorbent article 1 and stretched in different parts of the absorbent article 1, the elastic member 19 may deform different parts of the central portion and thereby, for instance, create an extension of the ridge-like elevation 20 in the rear portion 7, into the central portion. This is in order to further improve the anatomical fit against the user's body for an article with a ridge-like elevation which extends across both the central portion of the article and across the rear portion thereof, the ridge-like elevation in the end portion preferably has a steeper inclination towards the center line of the article than does the ridge-like elevation in the central portion, when seen from a long side of the article. To enhance the ridge-like elevation in the central portion, the absorbent core 4 may be slit either entirely or partially.

The invention should not be regarded as being limited to the herein-described embodiments, instead a number of further variants and modifications are conceivable within the scope of the claims. For instance, the invention comprises all types of absorbent articles, which are sized to be substantially accommodated in the groin area of a user. Furthermore, all conceivable combinations of the described embodiments are intended to be embraced by the invention.

The elastic member may be placed in or/and against any one of the layers that builds the absorbent article, dependent on desired features of the absorbent article, but from fastening and manufacturing point of view, it is advantageously fastened on the liquid-impervious layer.

The elastic member may comprise more than one elastic element, which together fulfil the same purpose as the single elastic member described in the embodiments above.

The absorbent article may also include an elastic member that runs through the entire article and that is split in two half circle shaped parts in the front portion, which split half circle shaped elastic parts give the article a cup-shaped part at the front portion of the absorbent article and a ridge-like elevation in at least the rear portion.

The elastic member may also be arranged in a loop in the front portion, which may or may not be pre-cup-shaped, and the arrangement of the elastic member in a loop contributes to give the front portion its cup shape.

The absorbent body may also comprise a first portion, which forms a longitudinal hump on the side of the absorbent article, which in use is intended to face a user. The first portion may consist of a material with high absorption capacity, for instance absorbent fibers such as cellulose fluff pulp, rayon or the like, with or without super-absorbent material, absorbent foam or any of the above-described absorbent fiber materials. Furthermore, all conceivable types of blends and combinations of material layers may be used.

The absorbent body of the absorbent article may further comprise an absorption layer arranged between the hump and the liquid-impervious cover layer. The absorption layer may comprise an absorbent nonwoven material, tissue paper or any one of the above-mentioned absorbent materials and may be designed with larger or smaller absorption capacity depending on the intended use of the absorbent article.

The absorbent article need not have a protruding edge nor does it need to have wings. The invention may thus be used on a number of different shapes of absorbent articles, for instance an oval shape or rectangular shape.

The invention claimed is:

1. An absorbent article which has a substantially elongated shape with a longitudinal direction and a transverse direction and has two side edges, a front edge and a rear edge, a front portion, a rear portion and a central portion between the front portion and the rear portion, said article further has a liquid-pervious cover layer and a liquid-impervious cover layer and an absorbent body, wherein a rear portion of the absorbent body comprises a layer that is split into a substantially Y-shaped body having a first leg and a second leg with a gap between the legs having an angle $\alpha$ defined between the first leg and the second leg, wherein said rear portion of the absorbent body begins at a change in inclination of the side edges with respect to a longitudinal center line of said article, wherein a center portion of the absorbent body is a primary receiving portion when a liquid is emitted on to the absorbent body, and wherein an elastic member is placed between the first leg and the second leg without overlapping said first and second legs, said elastic member essentially extends in the longitudinal direction.

2. Absorbent article according to claim 1, wherein the elastic member bends the rear portion in a substantially parabolic shape, deforming parts of the absorbent article that lies between the first leg and the second leg, thereby forming a ridge between the first leg and the second leg.

3. Absorbent article according to claim 2, wherein the elastic member runs along a center line of the absorbent article, from where the center line meets the rear edge, to a point beyond the point where the layer in the absorbent body is split into the two legs.

4. Absorbent article according to claim 2, wherein the elastic member runs along the center line, longitudinally along the entire absorbent article.

5. Absorbent article according to claim 4, wherein the elastic member is split into at least two elastic parts in the front portion.

6. Absorbent article according to claim 2, wherein the elastic member is placed in any of the layers that builds the absorbent article.

7. Absorbent article according to claim 2, wherein the angle $\alpha$ is between 10°–120°.

8. Absorbent article according to claim 2, wherein the length of the legs is 20–350 mm.

9. Absorbent article according to claim 2, wherein the length of the ridge is at least 10 mm.

10. Absorbent article according to claim 2, wherein the ridge has a top portion constituting an upper part of the ridge and that the width of the ridge is 0.1–20 mm at the top portion of the ridge.

11. Absorbent article according to claim 1, wherein the elastic member is attached to the article in a stretched state.

12. The absorbent article according to claim 11, wherein said first and second legs are substantially coplanar.

13. The absorbent article according to claim 1, wherein said angle $\alpha$ is in a transverse plane.

14. An absorbent article which has a substantially elongated shape with a longitudinal direction and a transverse direction and has two side edges, a front edge and a rear edge, a front portion, a rear portion and a central portion between the front portion and the rear portion, said article further has a liquid-pervious cover layer and a liquid-impervious cover layer and an absorbent body, wherein a rear portion of the absorbent body comprises a layer that is split into a substantially Y-shaped body having a first leg and a second leg with a gap between the first and second legs, said gap increasing from a proximal end to a distal end of said first and second legs, wherein said rear portion of the absorbent body begins at a change in inclination of the side edges with respect to a longitudinal center line of said article, and wherein an elastic member is placed between the first leg and the second leg without overlapping said first and second legs, said elastic member essentially extends in the longitudinal direction.

* * * * *